(12) United States Patent
Davies

(10) Patent No.: US 7,112,972 B2
(45) Date of Patent: Sep. 26, 2006

(54) GAUGE CALIBRATION

(75) Inventor: Mark Ian Davies, Oxford (GB)

(73) Assignee: Crown Packaging Technology, Inc., Alsip, IL (US)

( * ) Notice: Subject to any disclaimer, the term of this patent is extended or adjusted under 35 U.S.C. 154(b) by 0 days.

(21) Appl. No.: 10/520,422

(22) PCT Filed: Jun. 20, 2003

(86) PCT No.: PCT/EP03/06505

§ 371 (c)(1),
(2), (4) Date: Dec. 22, 2005

(87) PCT Pub. No.: WO2004/005841

PCT Pub. Date: Jan. 15, 2004

(65) Prior Publication Data

US 2006/0164103 A1    Jul. 27, 2006

(30) Foreign Application Priority Data

Jul. 10, 2002  (EP) .................. 02254834

(51) Int. Cl.
*G01R 27/26* (2006.01)
*G01R 35/00* (2006.01)
*G01C 25/00* (2006.01)

(52) U.S. Cl. .................. 324/671; 324/601; 702/97

(58) Field of Classification Search ........ 324/519, 324/512, 500, 716, 661, 662, 663, 658, 671, 324/699, 635, 644, 229, 230, 601; 73/1.13, 73/1.79; 702/85, 97, 158, 170; 250/251.2
See application file for complete search history.

(56) References Cited

U.S. PATENT DOCUMENTS

| | | | |
|---|---|---|---|
| 4,510,577 A * | 4/1985 | Tsujii et al. .................. 702/97 |
| 4,587,623 A * | 5/1986 | Regimand et al. ............ 702/90 |
| 4,996,658 A | 2/1991 | Baker |
| 5,138,268 A * | 8/1992 | Mulkey et al. .............. 324/671 |
| 5,293,132 A | 3/1994 | Koch |
| 5,612,782 A * | 3/1997 | Keranen et al. ......... 250/252.1 |
| 5,865,059 A * | 2/1999 | Alessandro .................. 73/159 |
| 6,020,264 A | 2/2000 | Lustig et al. |
| 6,025,787 A * | 2/2000 | Poduje et al. .......... 340/870.04 |
| 6,078,042 A * | 6/2000 | Fellows .................... 250/252.1 |
| 6,369,381 B1 * | 4/2002 | Troxler et al. ........... 250/252.1 |
| 6,617,861 B1 * | 9/2003 | Joshi .......................... 324/637 |
| 2002/0149360 A1 * | 10/2002 | Le .............................. 324/230 |

* cited by examiner

*Primary Examiner*—Anjan Deb
*Assistant Examiner*—Hoai-An D. Nguyen
(74) *Attorney, Agent, or Firm*—Diller, Ramik & Wight

(57) ABSTRACT

A method of calibrating a gauge in particular for the measurement of film thickness, uses a calibration variable to compensate for short term changes in probe tip condition, instead of a constant value. A calibration constant is based only on the dielectric constant for a coating such as lacquer, and is independent of the probe tip variable.

7 Claims, No Drawings

GAUGE CALIBRATION

CROSS-REFERENCE TO RELATED APPLICATION

This application is a 371 National Phase of the International Application No. PCT/EP03/06505 filed Jun. 20, 2003, claiming priority to a Foreign Application: EUROPEAN PATENT OFFICE (EPO) No. 02254834.1, filed Jul. 10, 2002.

BACKGROUND OF THE INVENTION

1. Field of the Invention

This invention relates to gauge calibration. In particular, but not exclusively, it relates to the calibration of gauges for measuring the weight/thickness of coatings such as lacquer applied to metals such as tinplate used in the can making trade.

2. Description of Prior Art

Capacitance based film weight gauges are known which are used for the measurement of dry film "weight". Whilst measurements taken by such known gauges are accurate, their calibration and stability over time is poor. In these gauges, a panel of known film weight is used to programme a selected channel to give the correct film weight when a measurement is taken. The panel allows the meter to be programmed with a factor K which relates the capacitance measured by the gauge to the film weight. This factor is a function of the dielectric constant of the lacquer such that the film weight is computed from the product of the capacitance and this factor K. The value obtained on the gauge is a linear correction of the capacitance measured and allows the measurement of the film weight of this particular lacquer on production sheet metal.

One major problem with this known system is that recalibration is time consuming and needs to be carried out independently for each channel of the gauge, typically 40 or more channels being used. As a panel is required for checking each of the 40+ channels which are programmed, this inevitably leads to infrequent recalibration. These panels are also not produced to a common, traceable standard and are prone to damage and consequent inaccuracy through repeated usage.

A further problem with known gauges is that there is no way of quantifying either the condition of the tip of the probe which is used together with the gauge, or any contamination of the probe tip.

SUMMARY OF THE INVENTION

This invention seeks to provide a method of calibrating a film thickness gauge which is a single operation and which also compensates for any deterioration in probe tip condition.

According to the present invention, there is provided a method of calibrating a gauge for measuring film thickness/weight, the gauge including a probe, the method comprising the steps of:

(a) determining a universal calibration constant for a material from a first standard having a known capacitance and weight;

(b) measuring the weight of a second standard of known weight;

(c) calculating the difference between the measured weight and the known weight of the second standard to obtain a calibration variable; and either (c) resetting the calibration variable so that the measured weight of the second standard corresponds to its known weight, thereby recalibrating the gauge, or (d) cleaning the tip of the probe.

DETAILED DESCRIPTION OF THE PREFERED EMBODIMENTS

The Applicant has recognised that the factor K of known systems is not a true constant. In practice, this factor K comprises one true universal calibration constant comprising $K_{lacquer\ dielectric}$ and a calibration variable $K_{probe\ tip}$ which compensates for short term changes in the condition of the probe tip. Prior to this invention, degradation of probe tip was considered to be adequately compensated for by cleaning of the probe tip and was therefore combined with the calibration constant as a single factor K for measurement purposes.

The calibration constant is a factor derived for each lacquer which relates the dielectric of the lacquer to that of a standard material used for calibration. Once determined, the value is fixed and is a universal calibration constant which is the same for this material in every plant, independent of location. This standard therefore does not require storage on site except as a constant value "stored" in a computer database or programme, for example. There is thus no requirement to hold a library of standards on site, as required by prior art gauges. Furthermore, as this standard is a true constant, the value of the standard does not require rechecking when each film weight measurement is taken.

The calibration variable $K_{probe\ tip}$ is determined before each sheet is measured by checking the value obtained from a stable and robust standard which is held with the gauge in the factory or on site. In one preferred embodiment of the invention, this standard is a laminate and may ideally include a layer of polyethylene terephthalate (PET) which is robust and has similar electrical properties to conventional coatings. Trials have also shown that the level of correlation of laminate standards performance with a range of lacquers is extremely high.

Clearly the use of a calibration variable is better able to correct for any probe tip degradation than the visual inspection of prior art gauges. This single robust second standard is held on site and enables regular calibration of the gauge and/or before each film weight measurement, thus maximising the accuracy of the gauge. Recalibration of the gauge is carried out when the specified value of the second standard cannot be achieved by cleaning of the probe tip.

Preferably the invention further comprises the steps of (e) placing a capacitance of known value in series with the gauge; and (f) measuring the capacitance of a circuit formed by the gauge and known capacitor to obtain an indication of the degree of deterioration of the probe tip and any need for resetting the value of the calibration variable.

Known gauges have no means of recording deterioration of the probe tip over an extended period of time and so are unable to detect when a probe tip might need changing. By using a fixed capacitor to check the reading on the gauge independently of the condition of the probe tip, cumulative recalibrations can be tracked. In this instance, the gauge measurement is directly proportional to the value of the calibration variable as the capacitance and calibration constant are fixed. The calibration variable is, in turn, related to probe tip condition.

By using a panel comprising a known standard film to recalibrate the gauge and by checking the probe tip for degradation using a standard capacitor, the method of the present invention provides a system which enables one-off calibration for films and lacquers on-site, in factory environments or in the laboratory, as required. By checking for probe tip damage, calibration for drift in readings due to probe condition is applicable to all readings and can be set "globally" on a single channel using a single standard.

EXAMPLE 1

The lacquer calibration constant for a lacquered panel was determined from panel standards as 0.233 and this value was saved in a computer data base. The calibration variable of a laminate standard was determined from master standards as 75. Probe tip condition was checked by use of a capacitor placed in series with the gauge. Capacitance readings for a film were converted to film weight and multiplied by 0.233 to give actual film weights. Resultant data was stored.

Any change observed in the lacquer standard was also observed in the laminate standard. Any changes were found to be due to probe tip contamination rather than drift in lacquer properties. By referring to a measurement of pure capacitance, any degradation of the probe tip was assessed and the need for replacement probe tip rather than continued recalibration was determined.

Although preferred embodiments of the invention have been specifically illustrated and described herein, it is to be understood that minor variations may be made in the method without departing from the spirit and scope of the invention, as defined by the appended claims.

What is claimed is:

1. A method of calibrating a gauge for measuring film weight, the gauge including a probe, the method comprising the steps of:
    (a) determining a universal calibration constant for a material from a first standard having a known capacitance and weight;
    (b) measuring the weight of a second standard of known weight;
    (c) calculating the difference between the measured weight and the known weight of the second standard to obtain a calibration variable; and
    either (d) resetting the calibration variable so that the measured weight of the second standard corresponds to its known weight, thereby recalibrating the gauge, or
    (e) cleaning the tip of the probe.

2. The method according to claim 1, in which the second standard is a laminate.

3. The method according to claim 1 in which the second standard includes a layer of polyethylene terephthalate.

4. The method according to claim 1, further comprising the steps of:
    (e) placing a capacitance of known value in series with the gauge; and
    (f) measuring the capacitance of a circuit formed by the gauge and known capacitor to obtain an indication of the degree of deterioration of the probe tip.

5. The method according to claim 2 in which the second standard includes a layer of polyethylene terephthalate.

6. The method according to claim 2, further comprising the steps of:
    (e) placing a capacitance of known value in series with the gauge; and
    (f) measuring the capacitance of a circuit formed by the gauge and known capacitor to obtain an indication of the degree of deterioration of the probe tip.

7. The method according to claim 3, further comprising the steps of:
    (e) placing a capacitance of known value in series with the gauge; and
    (f) measuring the capacitance of a circuit formed by the gauge and known capacitor to obtain an indication of the degree of deterioration of the probe tip.

* * * * *